United States Patent [19]

Boudouris et al.

[11] 4,028,518

[45] June 7, 1977

[54] DEVICE FOR SUPERFICIALLY HEATING AN ADJACENT BODY

[75] Inventors: Georges Boudouris, Grenoble; Grégoire Kalopissis, Neuilly-sur-Seine; Jean-Luc Leveque; Paul Roussopoulos, both of Paris, all of France

[73] Assignee: L'Oreal, Paris, France

[22] Filed: June 13, 1975

[21] Appl. No.: 586,748

[30] Foreign Application Priority Data

June 18, 1974 Luxembourg .................... 70345

[52] U.S. Cl. .............................. 219/10.81; 128/413
[51] Int. Cl.² ........................................ H05B 9/04
[58] Field of Search ................ 219/10.55 R, 10.81, 219/10.57; 128/404, 405, 406, 413, 399, 303.12, 303.13, 362

[56] References Cited

UNITED STATES PATENTS

| | | | |
|---|---|---|---|
| 2,130,758 | 9/1938 | Rose | 128/413 |
| 2,130,759 | 9/1938 | Rose | 128/413 |
| 2,190,712 | 2/1940 | Hansen | 128/413 |
| 2,223,447 | 12/1940 | Hathaway | 128/413 |
| 2,549,399 | 4/1951 | Tawney | 128/413 |
| 2,783,346 | 2/1957 | Warren | 219/10.81 |
| 2,923,801 | 2/1960 | Ellsworth | 219/10.81 |
| 3,403,359 | 9/1968 | Manwaring | 219/10.81 |
| 3,760,148 | 9/1973 | Boudouris et al. | 219/222 |
| 3,841,305 | 10/1974 | Hallgren | 219/10.57 |
| 3,863,653 | 2/1975 | Boudouris et al. | 219/10.55 R |

*Primary Examiner*—Arthur T. Grimley
*Attorney, Agent, or Firm*—Brisebois & Kruger

[57] ABSTRACT

Device for superficially heating an adjacent body comprising a high frequency resonator means for producing an electromagnetic field inside said resonator at the resonant frequency of said resonator when said device is adjacent a surface to be heated, and means for conducting energy from said field to radiating means outside said resonator.

8 Claims, 7 Drawing Figures

U.S. Patent June 7, 1977 Sheet 1 of 2 4,028,518
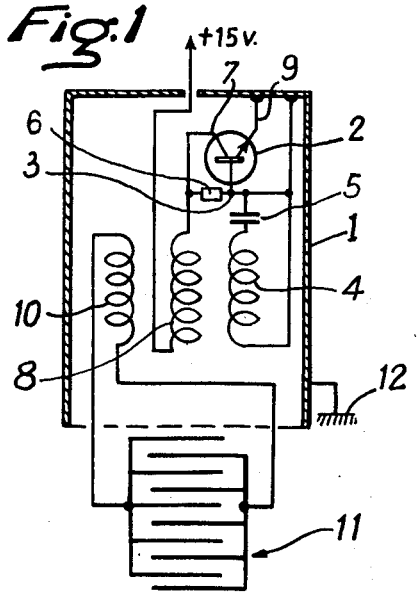
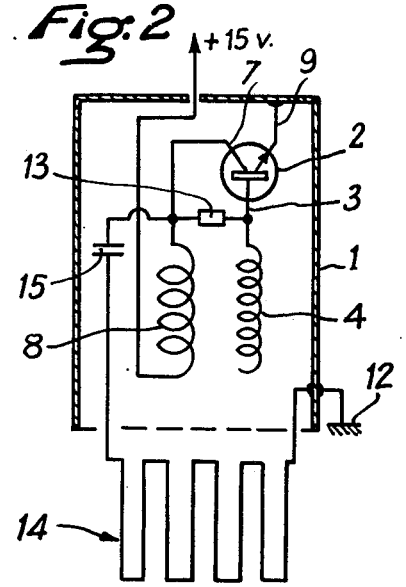
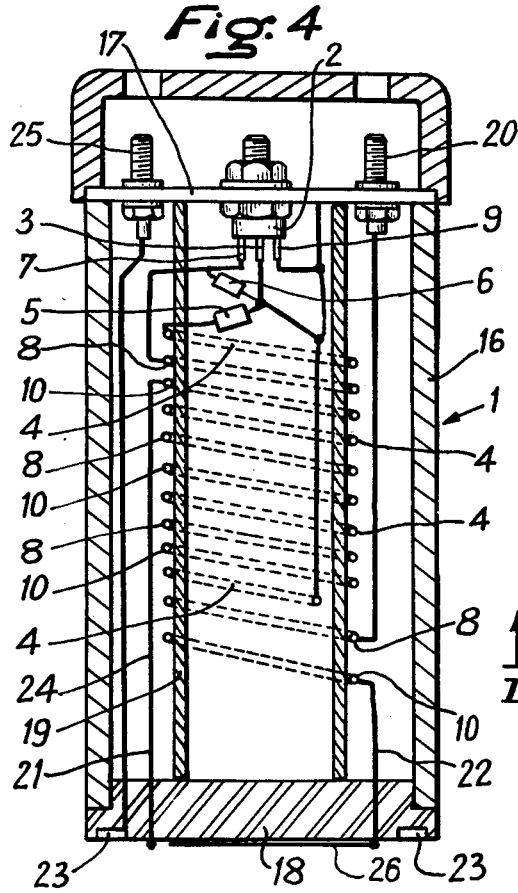
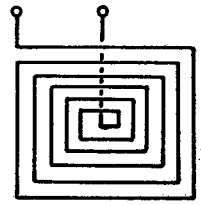
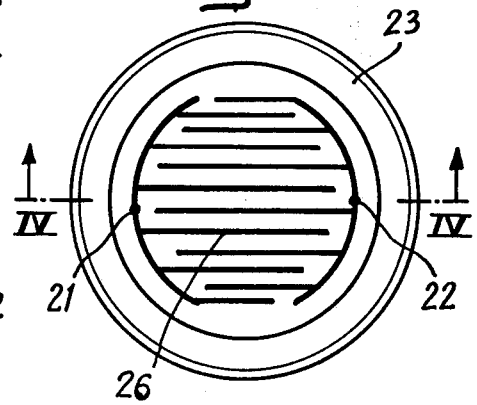

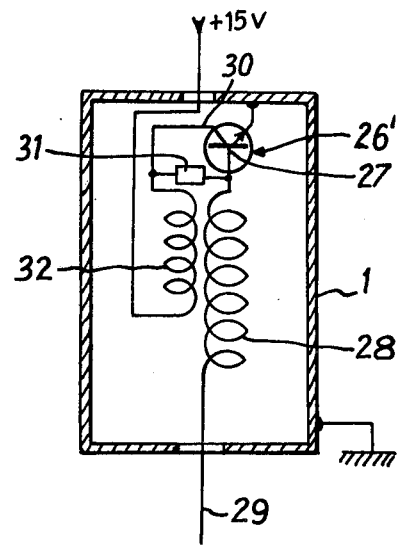
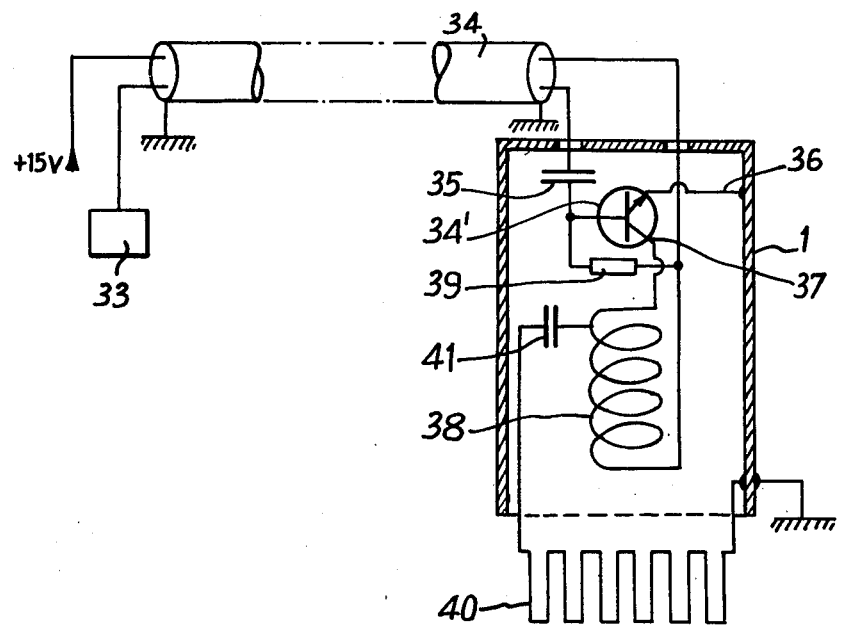

DEVICE FOR SUPERFICIALLY HEATING AN ADJACENT BODY

SUMMARY OF THE INVENTION

This invention relates to a new device for superficially increasing the temperature of a body, for example, the skin, by applying thereto a high frequency electromagnetic field.

The device according to the present invention has the property of requiring only low power and being particularly efficient, so as to avoid practically all waste of energy.

Moreover, the device according to the invention makes it possible to provide a superficial treatment, that is to say it develops heat only at the surface or in the immediate vicinity of the surface of the body against which it is applied.

Devices have already been designed for treating the hair by subjecting it to the action of a high frequency electromagnetic field. One such device consists of an electrically conductive jacket forming a resonator, means seated inside said jacket to receive or support the hair, coupling means for distributing electromagnetic energy at high frequency inside the jacket, and means inside or immediately adjacent the jacket which produces all or the major part of the electromagnetic energy dissipated inside the resonator.

In one embodiment of this device the coupling member which diffuses the electromagnetic energy inside the jacket is in the form of a coil which is also used in the oscillating circuit producing the high frequency waves.

In this device the bodies to be heated are placed inside the resonator around the winding which constitutes the coupling member.

The present invention is distinguished from the foregoing device by the fact that, in order to produce superficial heating, the high frequency electromagnetic waves are not used inside the jacket constituting the resonator, but are used outside thereof.

It is the object of the present invention to provide, as a new article of manufacture, a device which makes it possible to increase the superficial temperature of a body such as the skin, characterized by the fact that it comprises a resonator consisting of an electrically conductive jacket which is closed or substantially closed, in the electromagnetic sense of the term, and contains therewithin a coil emitting high frequency electromagnetic energy and a coupling member for adapting the high frequency energy to the resonator, together with an applicator circuit which conducts the energy produced inside the envelope to applicator means outside the jacket, preferably at the bottom thereof.

The phrase "increasing the superficial temperature of a body" is intended to include increasing the temperature of the body not only on its surface, but also in the neighborhood of its surface to a certain depth determined by the penetration of the electromagnetic radiation diffused in the body by the applicator.

In a first embodiment of the invention the applicator circuit consists of a winding subject to the action of a high frequency electromagnetic field which is located inside the resonator, said winding being connected to an applicator consisting, for example, of a capacitance having interleaved plates or a simple wand connected to the winding permitting a localized heating.

In a first embodiment of the invention the electromagnetic energy emitted inside the jacket is matched to the resonant frequency of the resonator only when a body which is to be treated is brought into the vicinity of the applicator.

When the applicator of energy (consisting for example of a capacitance having interleaved plates) is approached by the hand, the resonator is coupled, that is to say the frequency of the electromagnetic energy emitted inside the jacket is adpated to the resonant frequency of the resonator.

In other words, in the first embodiment, the resonant frequency of the electromagentic energy which is propagated inside the resonator is a function of the presence or absence of the body to be treated in the neighborhood of the applicator.

This results in automatic matching of the frequency, and leads to the consumption of energy only when the desired heat treatment is being carried out.

In a second embodiment of the device according to the invention, a coupling member is mounted inside the jacket which has the effect of matching the frequency of the high frequency electromagnetic energy produced inside the jacket to the resonant frequency of the resonator.

In this embodiment, which operates at a fixed frequency which is the resonant frequency of the resonator, the high frequency electromagnetic energy is withdrawn from a point on a coil contained inside the jacket and transmitted through a condenser to an antenna which lies flat and constitutes the applicator.

When the antenna is not applied to the body to be treated the impedance of the circuit for applying the high frequency energy is high enough so that the consumption of energy of the device remains small.

When the antenna is applied against the body, for example, the skin, the impedance of the applicator circuit diminishes, and it then draws a substantial quantity of electromagnetic high frequency energy which is transformed into heat in the superficial zone of the skin which is reached by the radiation of the antenna.

In each of the embodiments it is possible to either produce the high frequency electromagnetic energy by means of a generator, preferably controlled by a quartz crystal positioned outside the envelope from low power energy transmitted through a coaxial cable and then amplified inside the jacket, or to produce this energy directly inside the jacket, in which case it is sufficient to simply supply a direct current or a low frequency current which may be modulated to permit the application of the high frequency energy in the form of a series of waves.

In an improved embodiment of the device according to the invention, it is also possible to locate in the vicinity of the applicator of high frequency energy, one or more electrodes supplied with low frequency electrical current or direct current, which makes it possible to provide a treatment of tissues in accordance with conventional techniques which is combined with superficial thermal treatment obtained in accordance with the invention.

The device according to the invention may be used in various ways. It may in particular be used to superficially increase the temperature of the skin so as to treat the latter or to cause its penetration by products which have previously been placed on the epidermis.

However, the depth of heating depends on the form and nature of the applicator as well as on the characteristics of the high frequency current.

In order that the invention may be better understood, several embodiments thereof will now be described, purely by way of illustration and example, with reference to the accompanying drawings in which:

FIG. 1 is a schematic view showing the circuitry of a first embodiment of the device according to the invention;

FIG. 2 is a circuit diagram of a second embodiment of the device according to the invention;

FIG. 3 illustrates one of the various possible types of antenna which may be used in the device of FIG. 2;

FIG. 4 is an axial sectional view taken through a device operating on the principle of FIG. 1;

FIG. 5 is a bottom plan view of the device of FIG. 4;

FIG. 6 is a circuit diagram illustrating a third embodiment of the device according to the invention; and FIG. 7 is a circuit diagram of yet another embodiment of a device according to the invention.

FIG. 1 schematically shows the jacket 1 of the resonator. This jacket defines a chamber which is cylindrical in shape and is electrically conductive or is coated with an electrically conductive layer, and is substantially closed in the electromagnetic sense of the term.

Inside the jacket 1 is a transistor 2 of the NPN type which may for example be a 2 N 3926 or 2 N 3927 transistor sold by the Motorola Company.

The base 3 of the transistor is connected on the one hand to ground at a point on the jacket 1 through an oscillating circuit consisting of a coil 4 and a condenser 5, and on the other hand, to the collector 7 through a resistance 6. The collector 7 of the transistor is connected to a source of +15 volt direct current through a coil 8. The emitter 9 of the transistor is connected to the jacket 1. A third coil 10 is connected at each of its ends to a capacitance having interleaved plates 11, as schematically indicated on FIG. 1.

The jacket is connected at 12 to ground and forms part of the electrical ground of the system.

It is clear that FIG. 1 represents a circuit diagram of the device and not its concrete embodiment. In particular, in practice, the coils 4, 8 and 10 are positioned so as to mutually influence each other and they are preferably concentric with or without interfitting between the turns of different coils.

In like manner the applicator which consists of a capacitance having interleaved plates has been shown in the plane of the figure, but it is obvious that the capacitance, which has a flattened structure, lies in the plane against which the body to be treated by high frequency radiation will be applied.

FIG. 2 shows another embodiment of the device according to the invention. FIG. 2 shows the jacket 1 which is connected to ground 12 as in the case of FIG. 1. This jacket contains a transistor 2 which may be of the type indicated in the description of FIG. 1. Base 3 of the transistor 2 is connected to the winding 4', the other end of which is free. The base is also connected to the collector through the resistance 13.

The collector 7 is also connected to the +15 volt DC source through the winding 8'.

The emitter 9 is connected to ground through the jacket 1.

The applicator consists of an antenna plate 14 connected to ground 12 and to the collector 7 of the transistor 2 through a capacitance 15. The values of the different components, and especially of the coils 4 and 8, are so selected as to produce an electromagnetic current at a frequency which corresponds to the resonant frequency of the jacket.

The value of the capacitance 15 is such that when the antenna 14 is not placed in the vicinity of the epidermis which is to be treated the impedance of the applicator circuit constituted by the antenna 14 and the capacitance 15 is so high that only a very small portion of the available energy is radiated by the antenna 14.

On the contrary, when the antenna 14 is applied to the skin, the impedance of the applicator circuit decreases very substantially and the high frequency magnetic energy which is generated inside the resonator radiates into the skin, which undergoes an increase in temperature.

It will be seen that, in the second embodiment of the device according to the invention, the energy generated inside the jacket has a fixed frequency which corresponds to the frequency of the resonator and that it is the variation in the impedance of the applicator circuit which causes the high frequency electromagnetic energy to flow outside the resonator.

When in the embodiment of FIG. 1, the application of the capacitance 11 to the skin acts through the coil 10 to produce a change in the frequency of the electromagnetic energy so that it becomes equal to the resonant frequency of the resonator.

It will nevertheless be seen that in these two cases the device according to the invention does not draw electromagnetic energy (that is to say, does not consume energy) except to the extent that the body to be treated is located in the vicinity of the applicator.

In the circuit diagrams of FIGS. 1 and 2 which have just been described, the applicators are schematically illustrated. In these two cases the applicators may be positioned outside the jacket and connected thereto by a coaxial cable, but they are preferably mounted on the lower surface of the jacket.

In the embodiment of FIG. 2 it also goes without saying that the coils 4 and 8 are advantageously concentric so that there is mutual inductance therebetween.

FIG. 3 schematically illustrates another embodiment of the antenna which constitutes the applicator shown in the circuit diagram of FIG. 2.

In the case of FIG. 3 the antenna is a wire wound in a spiral on a rectangular plate, but it is obvious that other embodiments of these applicators, and in particular of the antennae, may be utilized without thereby departing from the basic principle of the invention.

FIGS. 4 and 5 show in longitudinal section and bottom plan a device according to the first embodiment illustrated on FIG. 1. FIG. 4 shows a jacket 1 consisting of a metallic cylinder 16 provided at its upper end with an electrically conductive plate 17. At its lower end the jacket is closed by a plate of insulating material 18 which may be, for example, polytetrafluoroethylene.

A cylinder 19 made of an insulating material extends coaxially inside the jacket 1 and carries the various coils.

The plate 17 supports the transistor 2 as well as a terminal 20 which is adapted to be connected to the +15 volt source of direct current shown in FIG. 1. FIG. 4 also shows the condenser 5 and the resistor 6 which are connected respectively to the ends of the coil 4 and of the coil 8.

FIG. 4 also shows how the oscillator 7 is connected to one end of the coil 8, the other end of which is connected to the +15 volt terminal 20.

It also shows how the ends of the coil 10 are connected by conductors 21 and 22 to the applicator 26 constituted by the interleaved plates located on the external surface of the insulating plate 18.

It will be noted that the circular electrode 23 is connected through the conductor 24 to the terminal 25 which is supplied with direct current or low frequency current.

FIG. 5 clearly shows the circular electrode 23 as well as the ends of the conductors 21 and 22 which lead to the capacitance constituted by the interleaved plates. By way of example, the embodiment illustrated on FIG. 4 the circuit diagram of which is given on FIG. 1, may consist of the following components:

The transistor 2 is a transistor of the NPN type sold by the Motorola Company under the identification number 2 N 3926 or 2 N 3927.

The winding 4 consists of 14 turns having an average diameter of 32 mm and a pitch of 3.5 mm.

The winding 8 consists of 17 turns having an average diameter of 32 mm and a pitch of 3.5 mm.

The high frequency output coil 10 consists of 22 turns having an average diameter of 32 mm and a pitch of 3 mm.

In order to simplify the drawing, all the turns have been shown on FIG. 4. The biasing resistance 6 has a value of 6.2 $k\Omega$.

The connecting capacitance 5 has a value of 220 pF.

The resonant cavity has an internal diameter of 5 cm and a length of 10 cm.

The device for applying high frequency energy is a capacitance having interleaved plates and a surface area of 12 $cm^2$ consisting of 12 arms alternately distributed, with half connected to each end of the winding 10.

When under load, that is to say, when a hand is applied to the capacitance 11, the apparatus may draw a maximum power of 18 watts at a frequency of 9.7 MHZ which is the resonant frequency. This apparatus is capable of producing a substantial increase in the temperature of the skin by an application which may last only a few seconds.

The characteristics of an embodiment according to the diagram of FIG. 2 will now be described.

The transistor may be the same as the transistor of FIG. 1. The coil 4 consists of 16 turns having an average diameter of 35 mm and a pitch of 1 mm, the free end of the coil, which is not connected to the transistor, being located inside the cavity. The coil 8 consists of 17 turns having an average diameter of 30 mm and an average pitch of 2 mm. The biasing resistance 13 has a value of 5.8 $k\Omega$.

The capacitance 15 has a value of 22 1 nanofarads.

The inner diameter of the jacket is 5 cm and its length is 10 cm.

The constant frequency of operation of the device is 48 MHZ.

The power used is at most 18 watts and this power is only 0.01 watts when the antenna is not applied to the skin.

This apparatus makes it possible to produce a substantial increase in the temperature of the skin in several seconds.

In the embodiment schematically illustrated in FIG. 6 the jacket 1 connected to ground contains a transistor 26' of the NPN type. The base 27 of the transistor is connected, on the one hand, to a coil 28 which leads to a wand 29 projecting from the jacket 1 and constituting the applicator according to the invention and, on the other hand, to the collector 30 of the transistor through a resistance 31.

The collector 32 of the transistor is connected to a source of direct current, for example a +15 volt source, through a coil 38.

It should be appreciated that, in this embodiment, as a consequence of the particular structure of the applicator 29, it is possible to concentrate the electromagnetic energy produced inside the jacket at a localized point in contact with the wand 29 projecting from the coil 28. By way of example, the embodiment illustrated in FIG. 6 may have the following components:

The transistor 26' is a transistor of the NPN type sold by the Motorola Company under the identification number 2 N 2222. The coil 28 consists of 23 turns having an average diameter of 15 mm and a pitch of 2 mm. The coil 32 consists of seven turns having an average diameter 15 mm and a pitch of 2 mm. Resistance 31 has a value of 100 kilohms.

The envelope has an internal diameter of 5 cm and a length of 10 cm. This apparatus operates at a frequency of 12 MHZ, has a useful power of 1 to 2 watts permitting a substantial increase in the local temperature of the skin over a period of several seconds.

FIG. 7 shows another embodiment of the device according to the invention in which a resonator is supplied with high frequency low power electromagnetic energy furnished by an oscillator preferably controlled by a quartz crystal schematically indicated by reference numeral 33 and connected to the interior of the jacket by a coaxial cable 34. If necessary it is possible to preamplify the high frequency energy before its introduction into the jacket.

This high frequency low power electromagnetic energy is provided at the base of a power transistor 34' of the NPN type, located inside the jacket 1, through an adapter condenser 35. The emitter 36 of the transistor 34' is connected to the jacket 1 and thus to ground. The collector 37 of transistor 34 is connected to a coil 38, one end of which is connected to a DC source, for example +15 volts. In FIG. 7 the line supplying the 15 volt DC current and the line supplying the coil 38 inside the same cable 34 which is then a double coaxial cable.

However, it is also possible to provide distinct lines, on the one hand, to supply the direct current and on the other hand to supply the high frequency low power current.

The transistor 34' is connected to a resistor 39. The applicator of the device illustrated in FIG. 7 may be, for example, an antenna plate 40 identical to the antenna 14, of the embodiment of FIG. 2. This antenna 40 is connected on the one hand, to ground and, on the other hand, to coil 38 through a coupling condenser 41.

By way of example, the embodiment illustrated on FIG. 7 may comprise the following components:

The transistor 34' may be a power transistor of the NPN type such as sold for example by the Motorola Company under identification number 2 N 3927, or by the Radiotechnique Company under the identification number 2 N 3733.

In the first case, the useful power is about 15 watts and in the second case about 10 watts. The coil 38 consists of 18 turns having an average diameter of 30 mm and a pitch of 3.5 mm. The condenser 35 has a value of 4.7 nanofarads and the condenser 41 a value of 33 nanofarads.

The biasing resistance 39 of the transistor may vary in dependence on the power from a value of 2.2 kilohms to a value of 17 kilohms.

The oscillator 33 delivers energy at a frequency of 40 megahertz. The jacket has an internal diameter of 5 cm and a length of 10 cm. In this embodiment it is also possible to obtain a substantial increase in the temperature of the skin by an application which lasts only a few seconds.

It will of course be appreciated that the embodiments which have thus far been described have been given purely by way of illustration and example, and may be modified as to detail without thereby departing from the basic principles of the invention.

What is claimed is:

1. Device for increasing the superficial temperature of a body such as the skin, which comprises a resonator including an electrically conductive jacket which is substantially closed in the electromagnetic sense of the term, a coil inside said jacket for emitting high frequency electromagnetic energy, coupling means for matching said high frequency energy to the resonant frequency of the resonator, and an applicator circuit connected to conduct the energy produced inside the jacket to an applicator located outside the jacket.

2. Device as claimed in claim 1 in which the applicator circuit cmprises a coil inside the resonator subjected to the action of a high frequency electromagnetic field, and connected to said applicator.

3. Device as claimed in claim 2 in which the electrical properties of the electronic components of the device are such that the frequency of the electromagnetic energy is equal to the resonant frequency of the resonator when the applicator is positioned against a body which is to be heated.

4. Device as claimed in claim 1 in which the frequency of said electromagnetic energy corresponds to the resonant frequency of the resonator, while the applicator is connected through a condenser to a coil situated inside the jacket.

5. Device as claimed in claim 4 in which the impedance of the applicator circuit is so high that when the applicator is not against the body to be heated, the consumption of energy remains small.

6. Device as claimed in claim 1 in which the high frequency electromagnetic energy is derived from a generator outside the jacket.

7. Device as claimed in claim 1 in which the high frequency energy is generated inside the jacket.

8. Device as claimed in claim 1 which comprises, in addition to and adjacent the applicator, at least one electrode to which direct or low frequency electric currents may be supplied.

* * * * *